United States Patent [19]

Glen

[11] Patent Number: 5,330,676
[45] Date of Patent: Jul. 19, 1994

[54] CHLOROISOCYANURATE COMPOSITIONS WHICH RAPIDLY DISINTEGRATE

[75] Inventor: Jeffrey J. Glen, Meriden, Conn.

[73] Assignee: Olin Corporation, Stamford, Conn.

[21] Appl. No.: 951,952

[22] Filed: Sep. 28, 1992

Related U.S. Application Data

[63] Continuation-in-part of Ser. No. 648,949, Feb. 1, 1991, abandoned.

[51] Int. Cl.$^5$ ............................................. C01B 11/06
[52] U.S. Cl. ........................ 252/186.35; 252/187.34; 252/187.33
[58] Field of Search ................. 252/187.34, 187.33, 252/186.35

[56] References Cited

U.S. PATENT DOCUMENTS

| | | | |
|---|---|---|---|
| 3,213,029 | 10/1965 | Muchow et al. | 252/99 |
| 4,149,988 | 4/1979 | Brennan et al. | 252/187 C |
| 4,329,431 | 5/1982 | Youssef et al. | 435/253 |
| 4,380,501 | 4/1983 | Wojtowicz et al. | 252/186.24 |
| 4,444,316 | 4/1984 | Casberg et al. | 206/524.4 |
| 4,460,490 | 7/1984 | Barford et al. | 252/92 |
| 4,938,748 | 7/1990 | Yum et al. | 604/323 |
| 5,023,012 | 6/1991 | Buchan et al. | 25/181 |

FOREIGN PATENT DOCUMENTS 236900 5/1990 European Pat. Off.
739740 12/1972 South Africa.

Primary Examiner—Richard D. Lovering
Assistant Examiner—Joseph D. Anthony
Attorney, Agent, or Firm—F. A. Iskander

[57] ABSTRACT

Compositions in compressed form consisting essentially of a chloroisocyanurate compound and a disintegrating amount of a natural water-soluble gum selected from the group consisting of seed gums and microbial gums. The novel compositions when placed in water readily disperse the chloroisocyanurate compound to provide rapid and controlled increases in concentrations of available chlorine to water bodies such as swimming pools, spas, or hot tubs.

6 Claims, No Drawings

CHLOROISOCYANURATE COMPOSITIONS WHICH RAPIDLY DISINTEGRATE

This application is a continuation-in-part of U.S. application Ser. No. 07/648,949, filed on Feb. 1, 1991 and now abandoned.

BACKGROUND OF THE INVENTION

1. Field of Invention

This invention is related to compositions for sanitizing water bodies. More particularly, this invention is related to rapidly disintegrating compositions containing chloroisocyanurate compounds for sanitizing water bodies.

2. Description of Related Art

Trichloroisocyanuric acid is a known commercial compound for sanitizing water bodies such as swimming pools by providing available chlorine when dissolved in the water. When placed in a water body such as a swimming pool, trichloroisocyanuric acid dissolves slowly to release its available chlorine concentration and sanitize the water body. The solubility rate, for example, for tablets containing 14 grams of trichloroisocyanuric acid in water at 21° C. is about 0.27 gram per hour.

When increased solubility in water is required, other chloroisocyanurates, such as dichloroisocyanuric acid, or alkali metal salts of dichloroisocyanuric acid and their hydrates can be employed.

Alternatively, to increase the solubility rate of trichloroisocyanuric acid (TCCA), mixtures have been prepared with alkali metal salts, such as alkali metal carbonates and bicarbonates which react with TCCA in the presence of water to form an alkali metal dichloroisocyanurate.

Mixtures of trichloroisocyanuric acid with water soluble alkali metal salts such as alkali metal phosphates, including trisodium phosphate and tetrasodium phosphate, as well as sodium borate and sodium silicate are also known as sanitizing agents.

Separately, South African patent No. 73-9740, issued to Henkel & Cie teaches making readily soluble tablets by mixing dichloroisocyanuric acid or its alkali metal salts with starches such as potato, maize, wheat or rice starch, or starches which have been chemically partially reduced, peptized, or carboxymethylated. These tablets are used for the production of bleaching and disinfecting solutions, for example, for textiles, cleansing and rinsing preparations, alkaline bottle cleaners and mechanical dish washer preparations. The tablets can contain from 2.5 to 18 percent by weight of the starch and 80-97 percent by weight of sodium or potassium dichloroisocyanurate. It has been found, however, that in tablets oxidation of the starch occurs which reduces the stability of these mixtures.

BRIEF SUMMARY OF THE INVENTION

There is a need for chloroisocyanurate compositions in compressed forms which when placed in water readily disperse the chloroisocyanurate compound to provide rapid and controlled increases in concentrations of available chlorine to water bodies such as swimming pools, spas, or hot tubs.

This accomplishment has been achieved in compositions in compressed form consisting essentially of a chloroisocyanurate compound and a disintegrating amount of a natural water-soluble gum selected from the group consisting of seed gums and microbial gums.

DETAILED DESCRIPTION OF THE INVENTION

One component of the novel compositions of the present invention is a chloroisocyanurate compound. Chloroisocyanurate compounds which can be employed include trichloroisocyanuric acid (TCCA), having an available chlorine concentration in the range of from about 89-91.5%; and alkali metal salts of dichloroisocyanuric acid having an available chlorine concentration in the range of from about 56-63% Suitable alkali metals include sodium, potassium and lithium, with sodium being preferred. These chloroisocyanurate compounds are available commercially.

The second component of the composition is a natural water-soluble gum. Suitable as natural water-soluble gums are for example, seed gums including Guar gum and Locust Bean gum; and fermentation or microbial gums such as Xanthan gum. As the dispersing agent, the gums may be used individually or in mixtures. Natural water-soluble gums suitable as dispersing agents in the present invention may also be characterized as polysaccharide gums. Suitable polysaccharide gums are branched polysaccharides having regular short branches as exemplified by Guar gum, Locust Bean gum, and Xanthan gum. Suitable polysaccharide gums may be further identified as polyheteroglycans i.e. diheteroglycans such as Guar gum and Locust Bean gum, and triheteroglycan gums including Xanthan, and mixtures thereof. Polyheteroglycans include in their structures at least two different monosaccharides. Preferred embodiments of polyheteroglycans are Guar gum and Xanthan including mixtures thereof. The natural water-soluble gums are available commercially as industrial gums.

Excluded from use in the present invention are cellulose and starch derivatives including modified starches as well as synthetic starches.

Any amount of the natural water-soluble gums may be employed which will readily disintegrate the tablet and disperse the chloroisocyanurate compound when the compressed form of the composition is placed in water. For example, suitable amounts of the natural water-soluble gums include those in the range of from about 0.1 to about 15 percent by weight of the composition, preferably, from about 0.25 to about 10 percent by weight, and more preferably, from about 0.5 to about 5 percent by weight of the composition.

The novel compositions of the present invention are supplied in compressed forms such as, for example, tablets, rings, discs, sticks, briquettes, etc. The compressed forms may be produced by any suitable commercial methods using a homogenous mixture of the components. Preferred embodiments of the compressed form are tablets, discs and briquets, with tablets being particularly preferred.

When compressed forms of the compositions of the invention are placed in a body of water such as a swimming pool, the compressed form rapidly disintegrates to disperse small particles of the chloroisocyanurate compound in the water, the compositions thus provide controlled available chlorine concentrations in a body of water at increased rates of addition. While the rate of disintegration of the compressed form may be varied for different applications, when used in a swimming pool or spa, it is preferred that complete disintegration of the compressed form occurs within 30 minutes. Preferably disintegration of the compressed form occurs within from about 0.1 to about 10, and more preferably within from about 0.5 to about 5 minutes.

It is known that during storage chloroisocyanurate compounds undergo some decomposition with the formation of chlorine-containing gases. An accumulation of these chlorine-containing gases in the containers may result in their attack on the containers, causing embrittlement and loss of strength. Thus, containers for chloroisocyanurate compounds, e.g. drums, bottles, cans, etc., are tightly closed, but have not been, for example, hermetically sealed. This permits the release of gases of decomposition which may be formed, for example, during storage periods under conditions of elevated temperatures and humidity. Compressed forms of chloroisocyanurate compounds and the compositions of the present invention such as, for example, tablets may also be packaged in heat-sealed plastic bags or envelopes which may be shipped in boxes or cartons.

The chlorine-containing gases present in the heat sealed bags can promote the oxidation of some of the natural water-soluble gums employed in the novel compositions and deleteriously effect the disintegration rate of the compositions of the present invention.

To prevent an accumulation of these chlorine-containing gases, the use of gas scavenger agents is employed. Suitable gas scavenger agents include alkaline earth metal sulfates as described, for example, in U.S. Pat. No. 4,149,988 issued to J. P. Brennan et al. and mixtures of silica gel, carbon, and an alkali metal bicarbonate as taught in U.S. Pat. No. 4,444,316 issued to J. M. Casberg. These patents are incorporated in their entirety by reference. Any effective gas-scavenging amount of such agents may be used.

The novel compositions of the present invention are further illustrated by the following examples with no intention of being limited thereby. Unless otherwise indicated, all parts, percents, ratios and the like are by weight.

EXAMPLES 1-2

Mixtures of granular trichloroisocyanuric acid (TCCA) (CDB 90 ®Olin Corporation, Stamford, Conn.) with 2 parts by weight of Guar gum; and with 10 parts by weight of Guar gum (Aldrich Chemical Co., Milwaukee, Wis.), the trichloroisocyanuric acid being the only other component, were prepared by blending. A tabletting die (2.5 cm.dia.) was charged with 14 grams of the each of the mixtures and the mixtures compressed on a Carver press (Laboratory press, Model B, Sterling, Inc., Menomonee, Wis.) at 9,000 psi to produce a tablet of each mixture. To determine the disintegration rate of the tablets, a tablet was placed into an 8 oz. jar filled with tap water (25° C.) and the time measured for the tablet to completely disintegrate and disperse the TCCA to form a mound of trichloroisocyanuric acid granules at the bottom of the jar. The disintegration time of the tablets containing 2 percent by weight and 10 percent by weight of guar gum was less than 1 minute.

COMPARATIVE EXAMPLES A-D

Mixtures of granular trichloroisocyanuric acid (TCCA) (CDB 90 ®Olin Corporation, Stamford, Conn.) with unmodified corn, wheat, potato, and rice starches were prepared according to the method of Example 1-2. The mixture of unmodified corn starch contained 2.5 wt % corn starch and 97.5 wt % TCCA. The mixtures with wheat, potato and rice starches contained 2 wt % starch and 98 wt % TCCA. A tabletting die was charged with 14 grams of the each of the mixtures and the mixtures compressed at 9,000 psi to produce a tablet of each mixture. To determine the disintegration rate of the tablets, a tablet was placed into an 8 oz. jar filled with tap water (25° C.) and the time measured for the tablet to completely disintegrate and disperse the TCCA to form a mound of trichloroisocyanuric acid granules at the bottom of the jar. The disintegration time of the tablet containing 2.5 percent by weight of unmodified corn starch was 4 minutes. The tablets containing mixtures of TCCA with wheat starch, potato starch, and rice starch only partially disintegrated with the outer edges of the tablets crumbling but the rest of the tablet remaining in tact without any visible further disintegration for an extended period of time.

EXAMPLES 3-7

Mixtures of powdered TCCA and Guar gum at additive levels of 0.5%, 1%, 1.5%, 2%, and 2.5%. were prepared, the trichloroisocyanuric acid being the only other component. Each of the mixtures was compressed using the method of Example 1 at 10,000 psi into tablets containing 15 grams of the mixture. The disintegration time for a tablet of each of the mixtures was determined by placing the tablet in an 8 oz. jar filled with tap water (25° C.) and measuring the time for the tablet to completely disintegrate. Each of the tablets completely disintegrated within 3 minutes.

EXAMPLES 8-9

Tablets were prepared according to the method of Examples 1-5, containing 2% by weight of Guar gum and 98% by weight of TCCA, and 2% by weight of Xanthan gum and 98% by weight of TCCA. Six tablets of each mixture were placed in a covered petri dish and the dishes placed in an oven operated at a temperature of 40° C. for 92 days. Periodically a tablet of each mixture was removed from the oven and the disintegration time of the oven-dried tablets was measured using the method of Example 1. The disintegration times measured are given in Table I below:

TABLE I

| | Tablet Disintegration Times (seconds) | |
| --- | --- | --- |
| Example No. | 8. Guar Gum (2%) TCCA (98%) | 9. Xanthan Gum (2%) TCCA (98%) |
| Initial | 30 | 30 |
| 7 Days | 30 | 30 |
| 14 Days | 30 | 30 |
| 22 Days | 30 | 30 |
| 43 Days | 45 | 45 |
| 92 Days | 45 | 45 |

EXAMPLES 10-11

Tablets containing 2% Guar gum and 98% TCCA, and 2% Xanthan gum and 98% TCCA were placed individually in heat-sealed 2.5 mil high density polyethylene (HDPE) bags and placed in a storage room. The storage room was maintained at a temperature of 38° C. and 85% relative humidity for a period of 33 days. Periodically a tablet of each mixture was removed from its bag and the disintegration time of the tablets was determined using the method of Example 1. The disintegration times measured are given in Table II below:

TABLE II

| | Tablet Disintegration Times (seconds) | |
|---|---|---|
| Example No. | 10. Guar Gum (2%) TCCA (98%) | 11. Xanthan Gum (2%) TCCA (98%) |
| Initial | 50 | 60 |
| 11 Days | 60 | 120 |
| 33 Days | 150 | * |

*No disintegration of the tablet was observed

EXAMPLES 12–13

Tablets containing 2 wt % Guar gum and 98 wt % TCCA, and 2 wt % Xanthan gum and 98 wt % TCCA were placed in 2.5 mil high density polyethylene (HDPE) bags. Also placed in the HDPE bags was a packet having 32 g of a mixture of containing ca50% silica gel, ca17% carbon, and ca33% $NaHCO_3$ as a gas scavenging agent. The bags were heat-sealed and placed in a storage room. The storage room was maintained at a temperature of 38° C. and 85% relative humidity for a period of 33 days. Periodically a tablet of each mixture was removed from the oven and the and the disintegration time of the tablets was determined using the method of Example 1. The disintegration times measured are given in Table III below:

TABLE III

| | Tablet Disintegration Times (seconds) | |
|---|---|---|
| Example No. | 12. Guar Gum (2%) TCCA (98%) | 13. Xanthan Gum (2%) TCCA (98%) |
| Initial | 50 | 60 |
| 11 Days | 45 | 45 |
| 33 Days | 115 | 90 |

EXAMPLES 14–15

Mixtures were prepared by blending granular sodium dichloroisocyanurate (SDDC) (CDB 56 ®Olin Corporation, Stamford, Conn.) with 1 part by weight of Guar gum; and with 2 parts by weight of Guar gum, the sodium dichloroisocyanurate being the only other component. A tabletting die was charged with 20 grams of the each of the mixtures and the mixtures compressed at 10,000 psi to produce a tablet of each mixture. Each tablet was placed into an 8 oz. jar filled with tap water (25° C.) and the time measured for the tablet to completely disintegrate and disperse the SDDC. The disintegration time of the tablet containing 1 percent by weight was 4 minutes, and 2 percent by weight of guar gum was 3 minutes.

EXAMPLE 16

Tablets containing 2 wt % Guar gum and 98 wt % TCCA, were placed in a 2.5 mil high density polyethylene (HDPE) bag. Also placed in the HDPE bag was a packet having 70 g of a mixture of containing ca50% silica gel, ca17% carbon, and ca33% $NaHCO_3$ as a gas scavenging agent. The bag was sealed and placed on a shelf in a laboratory at ambient temperature. After 18 months, the bag was opened and the disintegration time measured using the method of Examples 1–5. The tablets completely crumbled within 3 minutes.

What is claimed is:

1. A composition in compressed form consisting essentially of a chloroisocyanurate compound and a disintegrating amount ranging from about 0.5 to about 5% by weight of Guar gum.

2. The composition of claim 1 in which said compressed form is selected from the group consisting of tablets, discs, and briquets.

3. The composition of claim 1 wherein said chloroisocyanurate compound is selected from the group consisting of trichloroisocyanuric acid and an alkali metal salt of dichloroisocyanuric acid.

4. The composition of claim 3 in which said chloroisocyanurate compound is trichloroisocyanuric acid.

5. The composition of claim 3 in which said chloroisocyanurate compound is an alkali metal salt of dichloroisocyanuric acid.

6. The composition of claim 5 in which said alkali metal is selected form the group consisting of sodium, potassium, and lithium.

* * * * *